US009615574B2

(12) United States Patent
Yin et al.

(10) Patent No.: US 9,615,574 B2
(45) Date of Patent: Apr. 11, 2017

(54) COMPOSITIONS OF DIBROMOMALONAMIDE AND THEIR USE AS BIOCIDES

(71) Applicant: Dow Global Technologies LLC, Midland, MI (US)

(72) Inventors: Bei Yin, Phoenixville, PA (US); Freddie L. Singleton, Collegeville, PA (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 15/037,553

(22) PCT Filed: Nov. 24, 2014

(86) PCT No.: PCT/US2014/067035
§ 371 (c)(1),
(2) Date: May 18, 2016

(87) PCT Pub. No.: WO2015/077682
PCT Pub. Date: May 28, 2015

(65) Prior Publication Data
US 2016/0295861 A1    Oct. 13, 2016

Related U.S. Application Data

(60) Provisional application No. 61/908,412, filed on Nov. 25, 2013.

(51) Int. Cl.
| | |
|---|---|
| A01N 57/00 | (2006.01) |
| A61K 31/66 | (2006.01) |
| A01N 37/18 | (2006.01) |
| A01N 37/30 | (2006.01) |
| C02F 1/50 | (2006.01) |
| C09D 5/14 | (2006.01) |
| A01N 57/20 | (2006.01) |
| C02F 103/00 | (2006.01) |
| C02F 103/10 | (2006.01) |
| C02F 103/14 | (2006.01) |
| C02F 103/42 | (2006.01) |
| C02F 103/34 | (2006.01) |

(52) U.S. Cl.
CPC ............. *A01N 37/18* (2013.01); *A01N 37/30* (2013.01); *A01N 57/20* (2013.01); *C02F 1/50* (2013.01); *C09D 5/14* (2013.01); *C02F 2103/002* (2013.01); *C02F 2103/008* (2013.01); *C02F 2103/10* (2013.01); *C02F 2103/14* (2013.01); *C02F 2103/34* (2013.01); *C02F 2103/42* (2013.01); *C02F 2303/20* (2013.01)

(58) Field of Classification Search
None
See application file for complete search history.

(56) References Cited

U.S. PATENT DOCUMENTS

| | | | |
|---|---|---|---|
| 2010/0286096 A1 | 11/2010 | Yin et al. | |
| 2011/0123641 A1* | 5/2011 | Gartner | A01N 37/30 424/616 |
| 2012/0177745 A1 | 7/2012 | Singleton et al. | |
| 2012/0178817 A1 | 7/2012 | Yin et al. | |
| 2012/0184588 A1 | 7/2012 | Singleton et al. | |
| 2012/0196836 A1 | 8/2012 | Yin | |
| 2013/0184341 A1 | 7/2013 | Yin et al. | |
| 2014/0023727 A1 | 1/2014 | Singleton et al. | |
| 2015/0018317 A1 | 1/2015 | Ji et al. | |

FOREIGN PATENT DOCUMENTS

| | | | | |
|---|---|---|---|---|
| CH | WO 2009015088 A2 * | 1/2009 | ............. | A01N 57/20 |
| JP | H0341009 A | 2/1991 | | |

OTHER PUBLICATIONS

Tanaka Y, et al; "Industrial antibacterial and bacteriostatic agent—comprising tetrakis(hydroxymethyl)phosphonium salt and further component, useful in e.g. pulp slurry, paint and metal processing oil", WPI Thomson, vol. 1999, No. 21 (1999) XP002546071.

Tanaka Y, et al, "An industrial bactericide—useful for process water in paper making plant, pulp slurry, cooling water etc.", WPI Thomson, vol. 1999, No. 43 (1999), XP002546000.

* cited by examiner

*Primary Examiner* — Jared D Barsky
(74) *Attorney, Agent, or Firm* — Tifani M. Edwards

(57) ABSTRACT

A biocidal composition comprising a synergistic ratio of 2,2-dibromomalonamide and hydroxymethyl-substituted phosphorus compound, and its use for the control of microorganisms in aqueous and water-containing systems.

4 Claims, No Drawings

COMPOSITIONS OF DIBROMOMALONAMIDE AND THEIR USE AS BIOCIDES

The invention relates to biocidal compositions and methods of their use for the control of microorganisms in aqueous and water-containing systems. The compositions comprise a synergistic blend of 2,2-dibromomalonamide and a hydroxymethyl-substituted phosphorus compound selected from the group consisting of tetrakis(hydroxymethyl)phoshponium salts and tris(hydroxymethyl)phosphine.

Water systems provide fertile breeding grounds for algae, bacteria, viruses, and fungi some of which can be pathogenic. Such microorganism contamination can create a variety of problems, including aesthetic unpleasantries such as slimy green water, serious health risks such as fungal, bacterial, or viral infections, and mechanical problems including plugging, corrosion of equipment, and reduction of heat transfer.

Biocides are commonly used to disinfect and control the growth of microorganisms in aqueous and water containing systems. However, not all biocides are effective against a broad spectrum of microorganisms and under a wide range of temperatures, and some are incompatible with other chemical treatment additives. In addition, some biocides do not provide microbial control over long enough time periods.

While some of these shortcomings can be overcome through use of larger amounts of the biocide, this option creates its own problems, including increased cost, increased waste, and increased likelihood that the biocide will interfere with the desirable properties of the treated medium. In addition, even with use of larger amounts of the biocide, many commercial biocidal compounds cannot provide effective control due to weak activity against certain types of microorganisms or resistance of the microorganisms to those compounds.

It would be a significant advance in the art to provide biocide compositions for treatment of water and water containing systems that provide one or more of the following advantages: increased efficacy at lower concentrations, compatibility with physical conditions and other additives in the treated medium, effectiveness against a broad spectrum of microorganisms, and/or ability to provide both short term and long term control of microorganisms.

The present invention provides a biocidal composition. The composition is useful for controlling microorganisms in aqueous or water containing systems. The biocidal composition comprises a synergistic blend of 2,2-dibromomalonamide and a hydroxymethyl-substituted phosphorus compound selected from the group consisting of tetrakis(hydroxymethyl)phoshponium salts and tris(hydroxymethyl)phosphine, wherein the weight ratio of 2,2-dibromomalonamide to the hydroxymethyl-substituted phosphorus compound is between 100:1 and 1:100. The present invention further provides a method for controlling microorganism growth and metabolic activities in an aqueous or water-containing system, the method comprising treating the aqueous or water-containing system with an effective amount of the biocidal composition.

The hydroxymethyl-substituted phosphorus compound of the present invention is selected from the group consisting of tetrakis(hydroxymethyl)phosphonium salts, including but not limited totetrakis(hydroxymethyl)phosphonium sulfate (THPS) and tetrakis(hydroxymethyl)phosphonium chloride (THPC) and tris(hydroxymethyl)phosphine (THP). More than one hydroxymethyl-substituted phosphorus compound may be present, in which case the biocide ratio is calculated from the total content of such compounds. Preferably the biocidal composition comprises a synergistic blend of 2,2-dibromomalonamide and a hydroxymethyl-substituted phosphorus compound selected from the group consisting of tetrakis(hydroxymethyl)phosphonium sulfate (THPS) and tetrakis(hydroxymethyl)phosphonium chloride and tris(hydroxymethyl)phosphine In a second aspect, the invention provides a method for controlling microorganisms in aqueous or water containing systems. The method comprises treating the system with an effective amount of a biocidal composition as described herein.

As noted above, the invention provides a biocidal composition and methods of using it in the control of microorganisms. The composition comprises a synergistic blend of 2,2-dibromomalonamide and a hydroxymethyl-substituted phosphorus compound. It has surprisingly been discovered that combinations of 2,2-dibromomalonamide and the hydroxymethyl-substituted phosphorus compound at certain weight ratios, are synergistic when used for microorganism control in aqueous or water containing media. That is, the combined materials result in improved biocidal properties than would be expected based on their individual performance. The synergy permits reduced amounts of the materials to be used to achieve the desired biocidal performance, thus reducing problems caused by growth of microorganisms in industrial waters and water containing systems while potentially reducing environmental impact and materials cost.

For the purposes of this specification, the meaning of "microorganism" includes, but is not limited to, bacteria, archaea, fungi, algae, and viruses. The words "control" and "controlling" should be broadly construed to include within their meaning, and without being limited thereto, inhibiting the growth, propagation or metabolic activity of microorganisms, killing microorganisms, disinfection, and/or preservation. In some preferred embodiments, "control" and "controlling" mean inhibiting the growth or propagation of microorganisms. In further embodiments, "control" and "controlling" mean the killing of microorganisms.

The term "2,2-dibromomalonamide" refers to a compound represented by the following chemical formula:

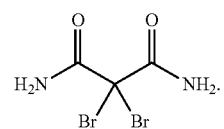

In some embodiments of the invention, the weight ratio of 2,2-dibromomalonamide to the hydroxymethyl-substituted phosphorus compound is between 100:1 and 1:100, alternatively, 1:3 and 1:16, alternatively between 1:4 and 1:16, alternatively between 1:3 and about 1:9. All ranges contained herein are inclusive and combinable.

The composition of the invention is useful for controlling microorganisms in a variety of aqueous and water containing systems. Examples of such systems include, but are not limited to, paints and coatings, aqueous emulsions, latexes, adhesives, inks, pigment dispersions, household and industrial cleaners, detergents, dish detergents, mineral slurries polymer emulsions, caulks and adhesives, tape joint compounds, disinfectants, sanitizers, metalworking fluids, construction products, personal care products, textile fluids such as spin finishes, industrial process water (e.g. oil and gas field injection/fracturing, flowback and produced water and fluids, pulp and paper water, cooling water), oilfield functional fluids such as drilling muds, completion and workover fluids, packer fluids, and hydrotest fluids, fuels, air washers, wastewater, ballast water, filtration systems, and swimming pool and spa water. Preferred aqueous systems are metal working fluids, personal care, household and industrial cleaners, industrial process water, and paints and coatings. Particularly preferred are industrial process water, paints and coatings, metal working fluids, and textile fluids such as spin finishes.

A person of ordinary skill in the art can readily determine, without undue experimentation, the effective amount of the composition that should be used in any particular application to provide microorganism control. By way of illustration, a suitable actives concentration (total for both 2,2-dibromomalonamide and the hydroxymethyl-substituted phosphorus compound) is typically at least about 1 ppm, alternatively at least about 3 ppm, alternatively at least about 7 ppm, alternatively at least about 10 ppm, alternatively at least about 30 ppm, or alternatively at least about 100 ppm based on the contamination level of the aqueous or water containing system. In some embodiments, a suitable upper limit for the actives concentration is about 1000 ppm, alternatively about 500 ppm, alternatively about 100 ppm, alternatively about 50 ppm, alternatively about 30 ppm, alternatively about 15 ppm, alternatively about 10 ppm, or alternatively about 7 ppm, based on the contamination level of the aqueous or water containing system.

The components of the composition can be added to the aqueous or water containing system separately, or pre-blended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

The following examples are illustrative of the invention but are not intended to limit its scope. Unless otherwise indicated, the ratios, percentages, parts, and the like used herein are by weight.

EXAMPLES

The synergism of the biocides combination of the present invention was determined using the method described by Kull, F. C, et al. in *Applied Microbiology* 9:538-541 (1961). The formula to calculate the synergistic index (SI) is $$Qa/QA+Qb/QB=SI$$

where
QA=concentration of compound A in ppm, acting alone produced an end point or if end point could not be established, the highest concentration tested will be used the as the end point for the calculation and the SI will be recorded in "less than or <" values
Qa=concentration of compound A in ppm, in the mixture, which produced an end point
QB=concentration of compound B in ppm, acting alone produced an end point or if end point could not be established, the highest concentration tested will be used the as the end point for the calculation and the SI will be recorded in "less than or <" values
Qb=concentration of compound B in ppm, in the mixture, which produced an end point Synergism within two biocides is demonstrated when the SI has a value less than 1. The mixtures showed an additive effect if SI is equal to 1 and antagonistic if SI is greater than 1.

Example 1: Synergistic Effect of DBMAL and THPS

Blends Against Anaerobic Bacteria—24 Hour Contact Time

Inside an anaerobic chamber (Bactron anaerobic chamber), a deoxygenated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na_2SO_4$, 43.92 mg of $Na_2CO_3$ in 1 L water, pH was adjusted to 7) was inoculated with *Desulfovibrio longus* ATCC 51456 to a final bacterial concentration of $10^7$ to $10^8$ CFU/mL. Aliquots of this cell suspension were then treated with DBMAL, THPS, and DBMAL/THPS blends, at selected active concentrations. After the treated cell suspensions were incubated at 40° C. for 24 hours, viable bacteria in each treated and untreated (control) cell suspensions were enumerated using a serial dilution method in Modified Baar's Medium (2.0 g of $MgSO_4$, 5.7 g of Sodium citrate.$2H_2O$, 1.0 g of $CaSO_4$, 1.0 g of $NH_4Cl$, 3.5 g of Sodium lactate, 1.0 g of Yeast extract, 0.5 g of $K_2HPO_4$, 0.1 g of Sodium Thioglycolate, 0.02 g of $Fe(NH_4)_2(SO_4)_2$, 20 g of NaCl in 1 L deionized water). The biocidal efficacy was determined by minimum tested biocide concentration for bacteria kill in the aliquots (MBC).

Table 1 summarizes the synergistic effect of each biocide and their blends, and the Synergy Index of each combination.

TABLE 1

Synergistic effect of DBMAL, THPS, and DBMAL/THPS blends against anaerobic bacteria and resulting Synergy Index values

| Ratio of DBMAL to THPS (active w/w) | MBC (ppm active) | | Synergy Index |
|---|---|---|---|
| | DBMAL | THPS | |
| 1:0 | 200.0 | 0.0 | |
| 2:1 | 100.0 | 50.0 | 1.50 |
| 1:1 | 50.0 | 50.0 | 1.25 |
| 1:2 | 50.0 | 100.0 | 2.25 |
| 1:4 | 6.3 | 25.0 | 0.53 |
| 1:8 | 3.3 | 25.0 | 0.52 |
| 1:16 | 1.5 | 25.0 | 0.51 |
| 0:1 | 0.0 | 50.0 | |

Example 2: Synergistic Effect of DBMAL and THPS

Blends Against Aerobic Bacteria—1 Hour Contact Time

Sterile salt solution (0.2203 g of $CaCl_2$, 0.1847 g of $MgSO_4$, and 0.2033 g of $NaHCO_3$ in 1 L water, adjust pH to 7.4) was inoculated with approximately $10^7$ CFU/mL of *Pseudomonas aeruginosa* ATCC 10145 and *Staphylococcus aureus* ATCC 6538.

Aliquots of the cell suspension were then treated with DBMAL, THPS, and combinations of these actives at selected concentrations.

After incubating at 37° C. for 1 hr, viable bacteria in each treated and untreated (control) cell suspensions were enumerated using a serial dilution method in Tryptic Soy Broth. The biocidal efficacy was determined by minimum biocide concentration for bacteria kill in the aliquots (MBC). Synergy Index was then calculated. Table 2 summarizes the MBC of each biocide and their blends, and the Synergy Index of each combination.

TABLE 2

Synergistic effect of DBMAL, THPS, DBMAL/THPS blends against aerobic bacteria in 1 hr contact time and resulting Synergy Index values

| Ratio of DBMAL to THPS (active w/w) | MBC (ppm active) DBMAL | MBC (ppm active) THPS | Synergy Index | p value in two tailed Z-test |
|---|---|---|---|---|
| 1:0 | >100.0 | | | |
| 9:1 | >90.0 | >10.0 | NA | 0 |
| 3:1 | >75.0 | >25.0 | NA | 0 |
| 1:1 | >50.0 | >50.0 | NA | 0 |
| 1:3 | 25.0 | 75.0 | <1.00 | 0 |
| 1:9 | 10.0 | 90.0 | <1.00 | 0 |
| 0:1 | 0.0 | 100.0 | | |

* P value < 0.05 means that there is significant difference between the Synergy Index and 1

The same test procedure in Example 2 was used to evaluate the biocidal efficacy of DBMAL, THPS and their blends against aerobic bacteria in a 2-hr contact assay. Table 3 summarizes the MBC of each biocide and their blends, and the Synergy Index of each combination.

Example 3: Synergistic Effect of DBMAL and THPS

Blends Against Aerobic Bacteria—2 Hour Contact Time

TABLE 3

Synergistic effect of DBMAL, THPS, and DBMAL/THPS blends agains aerobic bacteria in a 2-hr contact assay and resulting Synergy Index

| Ratio of DBMAL to THPS (active w/w) | MBC (ppm active) DBMAL | MBC (ppm active) THPS | Synergy Index | p value in two tailed Z-test |
|---|---|---|---|---|
| 1:0 | 77.8 | 0.0 | | |
| 9:1 | 95.0 | 10.6 | 1.62 | 3.65 |
| 3:1 | >37.5 | >112.5 | >4.29 | NA |
| 1:1 | >75.0 | >75.0 | >3.53 | NA |
| 1:3 | 16.7 | 50.0 | 1.91 | 0 |
| 1:9 | 3.0 | 26.7 | 0.94 | 0 |
| 0:1 | 0.0 | 29.6 | | |

As showed in Table 2 and Table 3, DBMAL in combination with THPS at 1:3 to 1:9 active weight ratios are synergistic against aerobic bacteria.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A biocidal composition comprising a synergistic blend of 2,2-dibromomalonamide and tetrakis(hydroxymethyl)phosphonium sulfate wherein the weight ratio of 2,2-dibromomalonamide to the tetrakis(hydroxymethyl)phosphonium sulfate is between 1:4 and 1:16 and further wherein the synergistic blend is synergistically effective against anaerobic bacteria.

2. The biocidal composition according to claim 1 which is: paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oil and gas field injection/fracturing, flowback and produced water and fluids as well as functional fluids, fuel, air washer, wastewater, ballast water, filtration systems, swimming pool or spa water.

3. A method for controlling microorganism growth and metabolic activities in an aqueous or water-containing system, the method comprising treating the aqueous or water-containing system with an effective amount of a composition according to claim 1.

4. The method according to claim 3 wherein the aqueous or water-containing system is paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oil and gas field injection/fracturing, flowback and produced water and fluids as well as functional fluids, fuel, air washer, wastewater, ballast water, filtration system, swimming pool or spa water.

* * * * *